United States Patent [19]

Kapa et al.

[11] Patent Number: 5,189,164

[45] Date of Patent: Feb. 23, 1993

[54] PROCESSES FOR THE SYNTHESIS OF SYN-(E)-3,5-DIHYDROXY-7-SUBSTITUTED HEPT-6-ENOIC AND HEPTANOIC ACIDS AND DERIVATIVES AND INTERMEDIATES THEREOF

[75] Inventors: Prasad K. Kapa, Parsippany; Kau-Ming Chen, Randolph, both of N.J.

[73] Assignee: Sandoz Ltd., Basel, Switzerland

[21] Appl. No.: 482,433

[22] Filed: Feb. 20, 1990

Related U.S. Application Data

[63] Continuation-in-part of Ser. No. 355,531, May 22, 1989, abandoned.

[51] Int. Cl.$^5$ .................. C07F 5/04; C07D 739/02; C07C 69/66; C07C 317/18
[52] U.S. Cl. ........................... 544/297; 544/318; 548/470; 548/376.1; 548/341.5; 552/105; 556/288; 566/55; 566/57; 566/60
[58] Field of Search ............... 558/288; 568/60, 55, 568/57; 548/300, 470; 552/105; 544/297, 318

[56] References Cited

U.S. PATENT DOCUMENTS 4,870,199  9/1989  Chen et al. .................... 552/105
4,983,759  1/1991  Inoue et al. .................... 552/105

*Primary Examiner*—C. Warren Ivy
*Assistant Examiner*—Raymond Covington
*Attorney, Agent, or Firm*—Gerald D. Sharkin; Richard E. Vila; Diane E. Furman

[57] ABSTRACT

A process for synthesizing syn-(E)-3,5-dihydroxy-7-substituted hept-6-enoic and heptanoic acids and derivatives and intermediates thereof from the corresponding keto-hydroxy compounds, which process comprises: providing a reaction medium comprising sodium borohydride and an alkoxydialkylborane compound; treating the keto-hydroxy compound with said reaction medium under conditions wherein a cyclic boronate ester is formed; and cleaving the cyclic boronate ester to obtain the dihydroxy product.

The product compounds, or derivatives thereof, are useful as anti-atherosclerotic agents.

29 Claims, No Drawings

PROCESSES FOR THE SYNTHESIS OF SYN-(E)-3,5-DIHYDROXY-7-SUBSTITUTED HEPT-6-ENOIC AND HEPTANOIC ACIDS AND DERIVATIVES AND INTERMEDIATES THEREOF

This application is a continuation-in-part of application Ser. No. 07/355,531 filed May 22, 1989 and now abandoned.

The present invention concerns a process for synthesizing compounds of the formula:

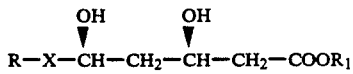

from compounds of the formula:

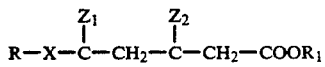

wherein
X is —CH$_2$—CH$_2$— or —CH=CH—,
Z$_1$ and Z$_2$ are either =O or

provided that Z$_1$ and Z$_2$ are not the same,

R$_1$ is an ester group inert to the reaction conditions, R$_1$ preferably being a physiologically acceptable hydrolyzable ester group, when the desired R is an organic radical having groups which are inert under reducing conditions, R preferably being selected from the group of Formula A, B, C, D, Ea, Eb, Ec, F, G, H, J, K, L, M, and N, i.e. as follows:

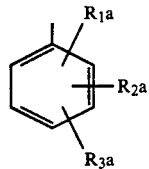

wherein
each of R$_{1a}$, R$_{2a}$ and R$_{3a}$ is independently hydrogen; halo; C$_{1-4}$alkyl, C$_{1-4}$haloalkyl, phenyl, phenyl substituted by halo, C$_{1-4}$alkoxy, C$_{2-8}$alkanoyloxy, C$_{1-4}$alkyl or C$_{1-4}$haloalkyl, or —OR$_{4a}$ in which R$_{4a}$ is hydrogen, C$_{2-8}$alkanoyl, benzoyl, phenyl, halophenyl, phenyl(C$_{1-3}$alkyl), C$_{1-9}$alkyl, cinnamyl, C$_{1-4}$haloalkyl, allyl, cycloalkyl(C$_{1-3}$alkyl), adamantyl(C$_{1-3}$alkyl) or substituted phenyl (C$_{1-3}$alkyl) each substituent of which is selected from the group consisting of halo, C$_{1-4}$alkoxy, C$_{1-4}$alkyl and C$_{1-4}$haloalkyl (the halogen atoms including fluoro and chloro and cycloalkyl including cyclohexyl);

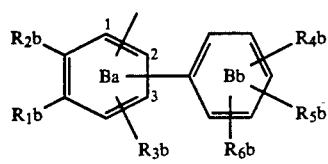

wherein R$_{1b}$ and R$_{2b}$ together form a radical of the formula:

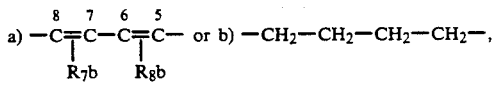

wherein
R$_{3b}$ is hydrogen, C$_{1-3}$alkyl, C$_{1-3}$alkoxy, trifluoromethyl, fluoro, chloro, phenoxy or benzyloxy, R$_{4b}$ is hydrogen, C$_{1-3}$alkyl, n-butyl, i-butyl, C$_{1-3}$alkoxy, n-butoxy, i-butoxy, trifluoromethyl, fluoro, chloro, phenoxy or benzyloxy, R$_{5b}$ is hydrogen, C$_{1-3}$alkyl, C$_{1-3}$alkoxy, trifluoromethyl, fluoro, chloro, phenoxy or benzyloxy, with the provisos that not more than one of R$_{4b}$ and R$_{5b}$ is trifluoromethyl, not more than one of R$_{4b}$ and R$_{5b}$ is phenoxy, and not more than one of R$_{4b}$ and R$_{5b}$ is benzyloxy; and R$_{6b}$ is hydrogen, C$_{1-2}$alkyl, C$_{1-2}$alkoxy, fluoro or chloro;

R$_{7b}$ is hydrogen, C$_{1-3}$alkyl, n-butyl, i-butyl, C$_{1-3}$alkoxy, n-butoxy, trifluoromethyl, fluoro, chloro, phenoxy or benzyloxy;

R$_{8b}$ is hydrogen, C$_{1-3}$alkyl, C$_{1-3}$alkoxy, trifluoromethyl, fluoro, chloro, phenoxy or benzyloxy;

with the provisos that not more than one of R$_{7b}$ and R$_{8b}$ is trifluoromethyl, not more than one of R$_{7b}$ and R$_{8b}$ is phenoxy, and not more than one of R$_{7b}$ and R$_{8b}$ is benzyloxy;

with the proviso that the free valence on ring Ba and ring Bb are ortho to each other;

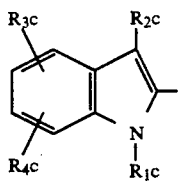

wherein one of R$_{1c}$ and R$_{2c}$ is phenyl substituted by R$_{5c}$, R$_6$ and R$_{7c}$ and the other is C$_{1-3}$alkyl, n-butyl or i-butyl, R$_{3c}$ is hydrogen, C$_{1-3}$alkyl, n-butyl, i-butyl, t-butyl, C$_{1-3}$alkoxy, -butoxy, i-butoxy, trifluoromethyl, fluoro, chloro, phenoxy or benzyloxy, R$_{4c}$ is hydrogen, C$_{1-3}$alkyl, C$_{1-3}$alkoxy, trifluoromethyl, fluoro, chloro, phenoxy or benzyloxy, with the provisos that not more than one of R$_{3c}$ and R$_{4c}$ is trifluoromethyl, not more than one of R$_{3c}$ and R$_{4c}$ is phenoxy, and not more than one of R$_{3c}$ and R$_{4c}$ is benzyloxy, R$_{5c}$ is hydrogen, C$_{1-3}$alkyl, n-butyl, i-butyl, t-butyl, C$_{1-3}$alkoxy, n-butoxy, i-butoxy, trifluoromethyl, fluoro, chloro, phenoxy or benzyloxy, R$_{6c}$ is hydrogen, C$_{1-3}$alkyl, C$_{1-3}$alkoxy, trifluoromethyl, fluoro, chloro, phenoxy or benzyloxy, with the provisos that not more than one of R$_{5c}$ and R$_{6c}$ is trifluoromethyl, not more than one of R$_{5c}$ and R$_{6c}$ is phenoxy, and not more than one of R$_{5c}$ and R$_{6c}$ is benzyloxy, and R$_{7c}$ is hydrogen, C$_{1-2}$alkyl, C$_{1-2}$alkoxy, fluoro or chloro;

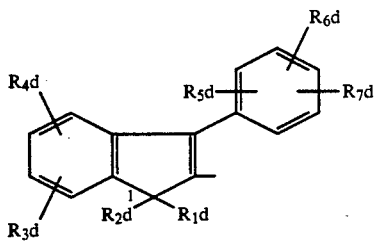
(D)

wherein

R₁d is hydrogen or primary or secondary $C_{1-6}$alkyl not containing an asymmetric carbon atom, and R₂d is primary or secondary $C_{1-6}$alkyl not containing an asymmetric carbon atom or R₁d and R₂d taken together are —(CH₂)m— or (Z)—CH₂—CH=CH—CH₂—, wherein m is 2,3,4,5, or 6;

R₃d is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, R₄d is hydrogen, $C_{1-3}$alkyl, $C_{1-3}$alkoxy, trifluoromethyl, fluoro, chloro, phenoxy or benzyloxy, with the provisos that not more than one of R₂d and R₃d is trifluoromethyl, not more than one of R₂d and R₃d is phenoxy, and not more than one of R₂d and R₃d is benzyloxy, R₅d is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, R₆d is hydrogen, $C_{1-3}$alkyl, $C_{1-3}$alkoxy, trifluoromethyl, fluoro, chloro, phenoxy or benzyloxy, with the provisos that not more than one of R₅d and R₆d is trifluoromethyl, not more than one of R₅d and R₆d is phenoxy, and not more than one of R₅d and R₆d is benzyloxy, R₇d is hydrogen, $C_{1-2}$alkyl, $C_{1-2}$alkoxy, fluoro or chloro;

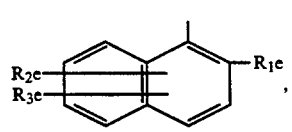
(Ea)

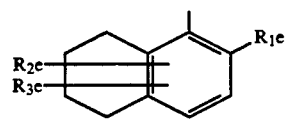
(Eb)

or

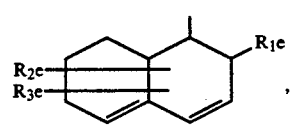
(Ec)

wherein each of R₁e, R₂e and R₃e is independently fluoro, chloro, hydrogen or $C_{1-4}$ alkyl, R₁e preferably being methyl;

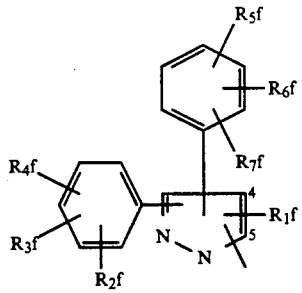
(F)

wherein

R₁f is $C_{1-6}$alkyl not containing an asymmetric carbon atom, each of R₂f and R₅f is independently hydrogen, $C_{1-3}$ alkyl, n-butyl, i-butyl, t-butyl, $C_{1-3}$alkoxy, n-butoxy, i-butoxy, trifluoromethyl, fluoro, chloro, phenyl, phenoxy or benzyloxy, each of R₃f and R₆f is independently hydrogen, $C_{1-3}$alkyl, $C_{1-3}$alkoxy, trifluoromethyl, fluoro, chloro, phenoxy or benzyloxy, and each of R₄f and R₇f is independently hydrogen, $C_{1-2}$alkyl, $C_{1-2}$alkoxy, fluoro or chloro, with the provisos that not more than one of R₂f and R₃f is trifluoromethyl, not more than one of R₂f and R₃f is not more than one of R₂f and R₃f is benzyloxy, not more than one of R₅f and R₆f is trifluoromethyl, not more than one of R₅f and R₆f is phenoxy, and not more than one of R₅f and R₆f is benzyloxy;

with the provisos that (i) the free valence of the pyrazole ring is in the 4- or 5- position, and (ii) the R₁f group and the free valence are ortho to each other;

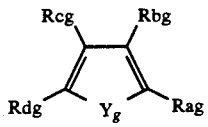
(G)

wherein

Rag is a single bond to X, Rbg is R₂g, Rcg is R₃g, Rdg is R₄g, and Yg is

—N—;
 |
 R₁g or

Rag is R₁g, Rbg is a single bond to X, Rcg is R₂g, Rdg is R₃g, and Yg is O, S or —N—;
 |
 R₄g R₁g, R₂g, R₃g and R₄g independently are $C_{1-6}$alkyl not containing an asymmetric carbon atom, $C_{3-7}$cycloalkyl or phenyl substituted by R₅g, R₆g and R₇g; or in the case of R₃g and R₄g additionally hydrogen, or for R₃g when Yg is O or S, and X is X', additionally Ga where Ga is as follows:

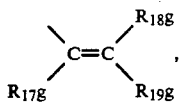
(Ga)

wherein
R$_{17g}$ is hydrogen or C$_{1-3}$alkyl,
and R$_{18g}$ and R$_{19g}$ are independently hydrogen, C$_{1-3}$alkyl or phenyl, each R$_{5g}$ is independently hydrogen, C$_{1-3}$alkyl, n-butyl, i-butyl, t-butyl, C$_{1-3}$alkoxy, n-butoxy, i-butoxy, trifluoromethyl, fluoro, chloro, bromo, phenyl, phenoxy or benzyloxy, each R$_{6g}$ is independently hydrogen, C$_{1-3}$alkyl, C$_{1-3}$alkoxy, trifluoromethyl, fluoro, chloro, bromo, phenoxy or benzyloxy, and each R$_{7g}$ is independently hydrogen, C$_{1-2}$alkyl, C$_{1-2}$alkoxy, fluoro or chloro, with the proviso that there may only be one each of trifluoromethyl, phenoxy and benzyloxy on each phenyl ring substituted by R$_{5g}$, R$_{6g}$ and R$_{7g}$;

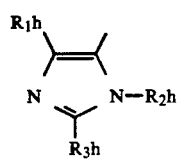
(H)

wherein
R$_1$h is C$_{1-6}$alkyl not containing an asymmetric carbon atom, C$_{3-7}$cycloalkyl, adamantyl-1, or phenyl substituted by R$_4$h, R$_5$h and R$_6$h, R$_2$h is C$_{1-6}$alkyl not containing an asymmetric carbon atom, C$_{3-7}$cycloalkyl, adamantyl-1, or phenyl substituted by R$_7$h, R$_8$h and R$_9$h, R$_3$h is hydrogen, C$_{1-6}$ alkyl not containing an asymmetric carbon atom, C$_{3-7}$cycloalkyl, adamantyl-1, styryl or phenyl substituted by R$_{10}$h, R$_{11}$h and R$_{12}$h, wherein each of R$_4$h, R$_7$h and R$_{10}$h is independently hydrogen, C$_{1-3}$alkyl, n-butyl, i-butyl, t-butyl, C$_{1-3}$alkoxy, n-butoxy, i-butoxy, trifluoromethyl, fluoro, chloro, bromo, phenyl, phenoxy, or benzyloxy, each of R$_5$h, R$_8$h and R$_{11}$h is independently hydrogen, C$_{1-3}$alkyl, C$_{1-3}$alkoxy, trifluoromethyl, fluoro, chloro, bromo, —COOR$_{17}$h, —N(R$_{19}$h)$_2$, phenoxy or benzyloxy, wherein R$_{17}$h is hydrogen, R$_{18}$h or M, wherein R$_{18}$h is C$_{1-3}$alkyl, n-butyl, i-butyl, t-butyl or benzyl, and M is as defined above, and each R$_{19}$h is independently C$_{1-6}$alkyl not containing an asymmetric carbon atom, and each of R$_6$h, R$_9$h and R$_{12}$h is independently hydrogen, C$_{1-2}$alkyl, C$_{1-2}$alkoxy, fluoro or chloro, with the provisos that not more than one substituent on each phenyl ring independently is trifluoromethyl, not more than one substituent on each phenyl ring independently is phenoxy, and not more than one substituent on each phenyl ring independently is benzyloxy,

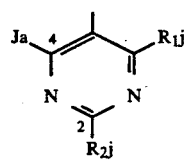
(J)

wherein
each of R$_1$j and R$_2$j is, independently C$_{1-6}$alkyl not containing an asymmetric carbon atom, C$_{3-6}$cycloalkyl or phenyl—(CH$_2$)$_m$—, wherein m is 0, 1, 2 or 3, and the phenyl group is unsubstituted or substituted by any of R$_3$j, R$_4$j and R$_5$j wherein R$_3$j-R$_5$j are as defined below;
or
R$_2$j is

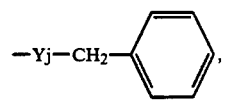

—N(R$_8$j)$_2$, or Ja
wherein
Yj is —O— or —S—;
each R$_8$j is independently C$_{1-4}$alkyl not containing an asymmetric carbon atom, or may form part of a 5, 6, or 7 membered ring Jb, said Ring Jb being substituted or unsubstituted and optionally also containing one or more hetero-atoms; and Ja is Ja' or Ja'' where Ja' is a heterocyclic group which is unsubstituted or substituted by one or two C$_{1-2}$alkyl or C$_{1-2}$alkoxy groups; and Ja'' is Ja''a or Ja''b

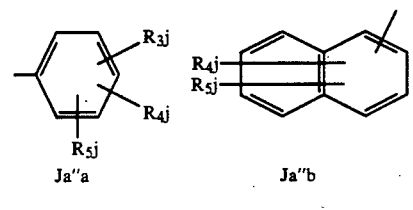

Ja''a          Ja''b wherein
R$_3$j is hydrogen, C$_{1-3}$alkyl, n-butyl, i-butyl, t-butyl, C$_{1-3}$alkoxy, n-butoxy, i-butoxy, trifluoromethyl, fluoro, chloro, phenoxy or benzyloxy, R$_4$j is hydrogen, C$_{1-3}$alkyl, C$_{1-3}$alkoxy, trifluoromethyl, fluoro, chloro, phenoxy or benzyloxy, and R$_5$j is hydrogen, C$_{1-2}$alkyl, C$_{1-3}$alkoxy, fluoro or chloro;

with the provisos that not more than one of R$_3$j and R$_4$j is trifluoromethyl, not more than one of R$_3$j and R$_4$j is phenoxy, and not more than one of R$_3$j and R$_4$j is benzyloxy;

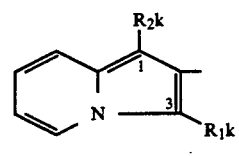
(K)

wherein
each of R$_1$k and R$_2$k is independently
(a) phenyl substituted by R$_2$k, R$_6$k and R$_7$k,
(b) hydrogen or a primary or secondary C$_{1-6}$alkyl not containing an asymmetric carbon atom;
(c) C$_{3-6}$cycloalkyl; or
(d) phenyl-(CH$_2$)$_m$—, wherein m is 1, 2 or 3,
wherein
R$_5$k is hydrogen, C$_{1-3}$alkyl, n-butyl, i-butyl, t-butyl, C$_{1-3}$alkoxy, n-butoxy, i-butoxy, trifluoromethyl, fluoro, chloro, phenoxy, or benzyloxy;

$R_6k$ is hydrogen, $C_{1-3}$alkyl, $C_{1-3}$alkoxy, fluoro, or chloro; and $R_7k$ is hydrogen, $C_{1-2}$alkyl, $C_{1-2}$alkoxy, fluoro, or chloro.

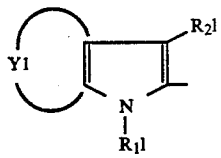
(L)

wherein

Y1 is —CH=CH—CH=N—, —C=CH—N=CH—, —CH=N—CH=CH— or —N=CH—CH=CH—

$R_1l$ is primary $C_{1-6}$alkyl not containing an asymmetric carbon atom; or isopropyl;

$R_2l$ is
(a) phenyl substituted by $R_5l$, $R_6l$ and $R_7l$,
(b) a primary or secondary $C_{1-6}$alkyl not containing an asymmetric carbon atom,
(c) $C_{3-6}$cycloalkyl or
(d) phenyl-$(CH_2)_m$—, wherein $R_5l$ is t-butyl, $C_{1-3}$alkoxy, n-butoxy, i-butoxy, trifluoromethyl, fluoro, chloro, phenoxy or benzyloxy;

$R_6l$ is hydrogen, $C_{1-3}$alkyl, $C_{1-3}$alkoxy, trifluoromethyl, fluoro, chloro, phenoxy or benzyloxy;

with the provisos that not more than one of $R_5l$ and $R_6l$ is trifluoromethyl, not more than one of $R_5l$ and $R_6l$ is phenoxy, and not more than one of $R_5l$ and $R_6l$ is benzyloxy, $R_7l$ is hydrogen, $C_{1-2}$alkyl, $C_{1-2}$alkoxy, fluoro or chloro, and m is 1, 2 or 3;

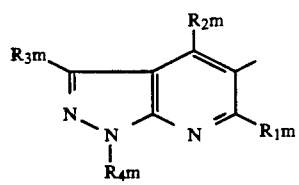
(M)

wherein $R_1m$ is $C_{1-6}$alkyl not containing an asymmetric carbon atom, $C_{5-7}$cycloalkyl, ($C_{5-7}$cycloalkyl)methyl, phenyl—$(CH_2)_m$—, pyridyl-2, pyridyl-3, pyridyl-4, thienyl-2, thienyl-3 or phenyl substituted by $R_5m$, $R_6m$ and $R_7m$, $R_2m$ is $C_{1-6}$alkyl not containing an asymmetric carbon atom, $C_{5-7}$cycloalkyl, ($C_{5-7}$cycloalkyl)methyl, phenyl-$(CH_2)_m$—, pyridyl-2, pyridyl-3, pyridyl-4, thienyl-2, thienyl-3 or phenyl substituted by $R_8m$, $R_9m$ and $R_{10}m$, with the proviso that not more than one of $R_1m$ and $R_2m$ is a member of the group consisting of pyridyl-2, pyridyl-3, pyridyl-4, thienyl-2, thienyl-3, phenyl substituted by $R_5m$, $R_6m$ and $R_7m$, and phenyl substituted by $R_8m$, $R_9m$ and $R_{10}m$, $R_3m$ is $C_{1-6}$alkyl not containing an asymmetric carbon atom, $C_{5-7}$cycloalkyl or phenyl substituted by $R_{11}m$, $R_{12}m$ and $R_{13}m$, $R_4m$ is $C_{1-6}$alkyl not containing an asymmetric carbon atom, $C_{5-7}$cycloalkyl or phenyl substituted by $R_{14}m$, $R_{15}m$ and $R_{16}m$, wherein each of $R_5m$, $R_8m$, $R_{11}m$ and $R_{14}m$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy or benzyloxy, each of $R_6m$, $R_9m$, $R_{12}m$ and $R_{15}m$ is independently hydrogen, $C_{1-3}$alkyl, $C_{1-3}$alkoxy, trifluoromethyl, fluoro, chloro, phenoxy or benzyloxy, and each of $R_7m$, $R_{10}m$, $R_{13}m$ and $R_{16}m$ is independently hydrogen, $C_{1-2}$alkyl, $C_{1-2}$alkoxy, fluoro or chloro, with the provisos that not more than one substituent on each phenyl ring independently is trifluoromethyl, not more than one substituent on each phenyl ring independently is phenoxy, and not more than one substituent on each phenyl ring independently is benzyloxy.

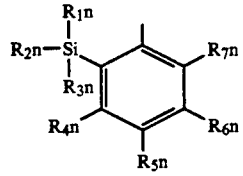
[N]

wherein each of $R_1n$, $R_2n$ and $R_3n$ is independently alkyl having from 1 to 4 carbon atoms; or phenyl which may be unsubstituted or substituted either by one or two alkyl or alkoxy groups having from 1 to 3 carbon atoms, or chloro, or by one fluoro, bromo or trifluoromethyl substituent;

$R_4n$ is hydrogen or alkyl having from 1 to 3 carbon atoms, e.g., methyl;

$R_5n$ is hydrogen, lower alkyl or alkoxy, halo, or trifluoromethyl; or phenyl, benzyl, or benzyloxy, wherein the aromatic portion may be unsubstituted, or substituted by up to two groups, one of which may be fluoro, bromo or trifluoromethyl, or one or two of which may be lower alkyl, alkoxy, or chloro;

$R_6n$ is a hydrogen atom, lower alkyl or alkoxy, halo, or trifluoromethyl; and $R_7n$ is a hydrogen atom, lower alkyl or alkoxy, halo or trifluoromethyl;

and any of $R_6n+R_7n$, $R_5n+R_6n$, or $R_6n+R_7n$ may constitute a 4 carbon radical, which is either —CH=CH—CH=CH— or —$(CH_2)_4$—, to form a ring which is substituted by $R_8n$ which is hydrogen, halo, lower alkyl or alkoxy;

provided that there be no more than one trifluoromethyl group, and no more than two bromo substituents present on the molecule.

The compounds of Formula I may be divided into thirteen groups, i.e., Groups IA-IN, depending upon the significance or R, i.e.;

IA when R=A.
IB when R=B,
IC when R=C,
ID when R=D,
IE when R=$E_a$, $E_b$ or $E_c$,
IF when R=F,
IG when R=G,
IH when R=H,
IJ when R=J,
IK when R=K,
IL when R=L,
IM when R=M, and
IN when R=N.

The compounds of Formula I, the corresponding δ-lactones, processes for converting a compound of Formula I wherein $R_1$ one significance or the corresponding compound wherein it has a different significance and/or into the corresponding δ-lactone are known. See, for example:

R = A U.S. Pat. Nos. 4,308,378 and 4,375,475;

R = B PCT Published Application WO 84/02903 and U.S. applications Ser. No. 06/570,584, filed Jan. 13, 1984 now abandoned, and Ser. No. 07/061,079 filed Jun. 10, 1987 and now abandoned R = C PCT Published Application WO 84/02131 and U.S. Pat. No. 4,739,073;

R = D PCT Published Application WO 86/03488 and U.S. applications Ser. No. 06/677,917, filed Dec. 4, 1984 and now abandoned, and Ser. No. 06/837,479, filed Mar. 7, 1986 and now R = Ea, (δ-lactone form only) U.S. Pat. No. 4,474,971 Eb or Ec;

R = F U.S. Pat. No. 4,613,610 and PCT Published Application WO 86/00307

R = G PCT Published Application WO 87/02662 and U.S. applications Ser. No. 06/919,275, filed Oct. 15, 1986 and now, and Ser. No. 06/945,428, filed Dec. 22, 1986 and now R = H U.S. Pat. Nos. 4,755,606 and 4,808,607;

R = J U.S. application Ser. No. 07/254,514 filed Oct. 6, 1988;

R = K U.S. Pat. No. 4,751,235;

R = L U.S. application Ser. No. 07/320,664 filed Mar. 8, 1989;

R = M U.S. Pat. No. 4,822,799;

R = N U.S. Pat. No. 4,588,715;

each of which is hereby incorporated by reference.

The compounds of Formula I and the corresponding δ-lactones are HMG-CoA reductase inhibitors, i.e., cholesterol biosynthesis inhibitors, and, therefore, they are useful for the treatment of hyperlipoproteinemia and atherosclerosis as disclosed in the aforementioned patents, published applications and applications which have been incorporated by reference.

The preferences for each of the variables in A, (, C, D, Ea, Eb, Ec, F, G, H, J, K, L, M, and N are as set forth in the aforementioned patents, published applications and applications which have been incorporated by reference.

By the term "physiologically acceptable and hydrolyzable ester group" is meant a group which, together with the —COO— radical to which it is attached, forms an ester group which is physiologically acceptable and hydrolyzable under physiological conditions to yield the corresponding carboxylic acid of the compound of Formula I (i.e. wherein $R_1$ is substituted by hydrogen) and an alcohol which itself is physiologically acceptable, i.e., non-toxic at the desired dosage level, particularly those which are free of centers of asymmetry.

$R_1$ is preferably $R_2$, where $R_2$ is $C_{1-4}$alkyl or benzyl, especially $R_2'$, where $R_2''$ is $C_{1-3}$ alkyl (e.g., ethyl), n-butyl, i-butyl, t-butyl, or benzyl, preferably isopropyl or t-butyl, especially t-butyl.

The compounds of Formula I may also be converted by conventional means into the corresponding salts, i.e. wherein $R_1$ is substituted by a physiologically acceptable cation, such as an alkali metal cation or ammonium, preferably sodium or potassium, and especially sodium. The compounds of Formula I may also be converted into the corresponding δ-lactones. Processes for so doing are disclosed in, for example, the aforementioned references that disclose various compounds of Formula I.

As set forth above, this invention is directed to a process for obtaining compounds of Formula I from compounds of Formula II.

Preferably in Formulae I and II, X is X', wherein X' is —CH=CH—, and most preferably $$\underset{H}{\overset{H}{\diagdown}} C = C \underset{H}{\overset{}{\diagup}} \quad (\text{i.e., (E)—CH=CH—})$$

Generally, when a hydroxy-keto compound of Formula II is reduced to a dihydroxy compound of Formula I, an additional center of asymmetry is generated. Consequently, when a racemic compound of Formula II is utilized, four stereoisomers (comprising two pairs of enantiomers, i.e. a pair of erythro and a pair of threo enantiomers) of the resulting compounds of Formula I are formed. Alternatively, when an optically pure compound of Formula II is utilized, two diastereoisomers (i.e. one erythro and one threo isomer) of the compound of Formula I are formed, e.g., the 3R,5S and 3S,5S diastereoisomers which result from reduction of the 5S hydroxy compound. Diastereoisomers may be separated by conventional means, such as by fractional crystallization, column chromatography, preparative thin layer chromatography or HPLC. The proportion of erythro to threo isomer obtained by these methods is usually variable and can be, e.g., up to about 98:1.

With the stereoselective process of the present invention, when a racemic compound of Formula II is used, only two stereoisomers (comprising the erythro pair of enantiomers) of the resulting compound of Formula I are formed almost exclusively. Alternatively, when an optically pure compound of Formula II is utilized, only one enantiomer of the compound of Formula I is formed almost exclusively, and this enantiomer is the corresponding erythro enantiomer. For example, the 3R,5S enantiomer results from the reduction of the 5S hydroxy compound wherein X is X'.

The proportion of erythro to threo isomer obtained with the process of the present invention is about 99.1:0.9 or higher, particularly about 99.5:0.5 or higher, especially about 99.7:0.3 or higher.

The term "stereoselective" as used herein thus means that the proportion of the erythro to the threo form is 99.1:0.9 or higher.

The stereoisomers of the compounds of formula I wherein X is X' (i.e. —CH=CH—) according to the present invention are the 3R,5S and the 3S,5R isomer and the racemate consisting of both of them, of which the 3R,5S isomer and the racemate are preferred.

The stereoisomers of the compounds of Formula I wherein X is —CH₂CH₂— according to the present invention are the 3R,5R and the 3S,5S isomer and the racemate consisting of both of them, of which the 3R,5R isomer and the racemate are preferred.

Conventional processes for reducing the keto group of a compound of Formula II have employed mild reducing agents such as sodium borohydride or a complex of t-butylamine and borane, in an inert organic solvent such as a lower alkanol, to yield a mixture of diastereomeric forms from the optically pure starting compound, or alternatively, the racemic diastereoisomers from the racemic starting material.

A three-step stereoselective reduction process has been used to obtain predominantly the erythro racemate from the racemic starting material. In the first step, a compound of Formula II is contacted either with a trialkylborane compound or a compound of Formula III:

$$R_4O-B-(R_3)_2$$

in which $R_4$ is allyl or lower alkyl having from 1 to 4 carbon atoms, preferably not tertiary, and $R_3$ is a primary or secondary alkyl having 2 to 4 carbon atoms, preferably not tertiary, in a reaction medium comprising an alcohol and tetrahydrofuran (THF).

In the second step of such processes, sodium borohydride (NaBH$_4$) is added to the reaction medium, and reaction proceeds with the reduction of the keto group, and in turn to the formation of the cyclic boronate ester and/or a boron complex of the compound of Formula I.

In the third step, the reaction mixture containing the cyclic boronate ester and/or boron complex is azeotroped with methanol or ethanol, or alternatively, is treated in an organic solvent with aqueous peroxy compounds, such as peroxide, e.g., hydrogen peroxide or a perborate, e.g., sodium perborate, or sodium percarbonate, to yield the resulting compounds of Formula I.

The aforementioned process is said to provide the erythro racemate with, e.g., about 98%, selectivity relative to the threo isomers. See Chen et al., Tetrahedron Letters 28, 155 (1987).

The process of the present invention comprises a method for steroselectively reducing racemic and optically pure compounds of Formula II to obtain almost exclusively the erythro isomer of Formula I. Advantageously, the reduction of the keto group of the compound of Formula II occurs virtually instantaneously.

The compounds of Formula I, i.e. the erythro isomers, are, additionally, provided in increased purity and may be further enriched to above 99% chemical purity by simple crystallization.

According to the first step of the process of the present invention (step (a)), a mixture is provided comprising an effective amount of the compound of Formula III and sodium borohydride, in a reaction medium comprising an alcohol and tetrahydrofuran. In the second step (step (b)), a compound of Formula II is treated with the react on medium of step (a) under conditions suitable for formation of a cyclic boronate ester and/or a boron complex of the compound of Formula I, wherein said cyclic boronate ester is formed. In the third step of the process (step (c)), the product obtained in step (b) is cleaved to obtain the corresponding compounds of Formula I.

Accordingly, reduction of compounds of Formula II by the process of this invention may conveniently be represented by the reaction scheme below, wherein R, $R_1$, $R_3$ and $R_4$ are as defined above, and wherein the compound of Formula IV(a) is a cyclic boronate ester, and the compound of Formula IV(b) is a boron complex, of the compounds of Formula I.

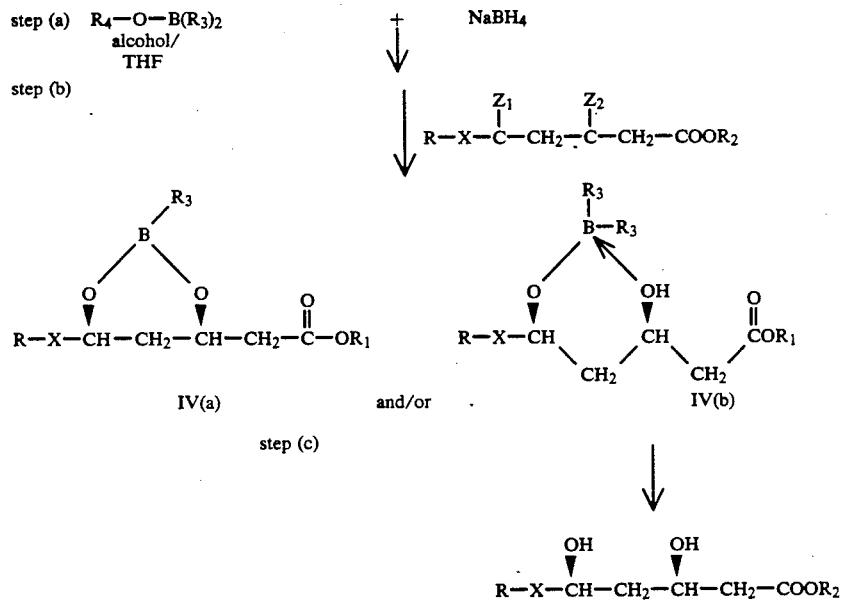

Step (a) is preferably carried out under essentially anhydrous conditions, and preferably in inert atmosphere, at temperatures of about $-100°$ to $+30°$ C., preferably at from about $-80°$ to $-60°$ C., especially about $-78°$ to $-70°$ C.

The reaction medium employed in step (a) comprises a mixture of alcohol/tetrahydrofuran, wherein the alcohol is of the formula $R_5OH$, in which $R_5$ is alkyl having from 1 to 4 carbon atoms, e.g. methyl or ethyl, preferably not tertiary. One of the products of step (a) may be $R_4OH$, derived from the compound III employed. However, it is not necessary that all or part of $R_5$ be the same as $R_4$.

The sodium borohydride should generally be present in at least equimolar amount with the compound of Formula II, and more preferably in slight excess, such as e.g. about 1.1:1 to 1.5:1 moles NaBH$_4$ per mole of ketone.

The molar ratio of the compound of Formula III to the compound of Formula II is at least about 0.5:1, and more preferably from about 0.7:1 to about 1.5:1 moles of borane compound per mole of ketone.

The next step, (b), wherein the keto-hydroxy compound of Formula II is treated with the reaction medium of step (a), is also preferably carried out at reduced temperatures, the internal temperature being maintained at about −100° to −40° C., especially from about −78° to −70° C. The compound of Formula II is preferably in a solvent such as alcohol/THF or THF. Preferably the reaction medium of step (a) and the solvent of the compound of Formula II which is added in step (b) are selected to make up a combined medium wherein the ratio (v/v) of alcohol to tetrahydrofuran is from about 1:3 to 1:6 of alcohol to THF, especially about 1:3 to 1:4.

Upon addition of the compound of Formula II, reduction of the keto group is exothermic and occurs rapidly, and therefore, addition of the keto compound is desirably staged in order to maintain an internal temperature in the range of about −78°−−70° C.

The reduction occurs almost instantaneously, to form a boron complex and/or a cyclic boronate ester of the compound of Formula I. The boron complex predominates prior to quenching. However, quenching converts the boron complex to the cyclic boronate ester.

The reaction mixture is quenched by adding, e.g., aqueous sodium bicarbonate, ammonium chloride or acetic acid, and the desired cyclic boronate ester compound is thus obtained.

In step (c), the reaction product of step (b) comprising predominantly the cyclic boronate ester compound is cleaved (or hydrolyzed) to yield the corresponding compound of Formula I. In one embodiment, this is carried out by azeotroping the reaction product of step (b), preferably with methanol or ethanol, at, e.g., from about 60° to 80° C., under essentially anhydrous conditions. Preferably, in an alternative embodiment, particularly where X is X', the reaction product of step (b) (having been neutralized by addition of sodium bicarbonate, $NaHCO_3$ and dissolved in an organic solvent, e.g., ethyl acetate), is cleaved by treating with aqueous (e.g., 30%) hydrogen peroxide, aqueous sodium perborate ($NaBO_3 \cdot 4H_2O$) or aqueous sodium percarbonate, to obtain the corresponding compound of Formula I. This is carried out initially at a reduced temperature, e.g., about +10° C., which is then allowed to rise to a moderate temperature, e.g., about 20°-30° C.

The resulting compound of Formula I may then be purified and recovered by various procedures including filtration and recrystallization.

Advantageously according to the process of the present invention, the reduction of the starting keto-hydroxy compounds occurs virtually instantaneously; and furthermore, reduction occurs in the absence of activators such as air or pivalic acid.

Since reducing conditions occur in practicing this invention, it is understood that any substituents or functions on the radical employed as R will be inert, i.e. that it will be free of substituents or functions which would be reactive or susceptible of alteration under such conditions, e.g. by known methods of masking or protecting such functions or introducing them at a later stage.

The (primary or secondary $C_{1-4}$alkoxy or allyloxy)-di-(primary $C_{2-4}$alkyl)boranes utilized in the process of the present invention are disclosed in Chen et al., *Tetrahedron Letters* 28, 155 (1987); and Chen et al, *Chemistry Letters*, pp. 1923-1926, 1987. However, they may be prepared in situ from the corresponding tri-(primary or secondary $C_{2-4}$alkyl)boranes by reaction with a primary or secondary $C_{1-4}$alkanol or allyl alcohol, the concentration of the former in the latter preferably being 0.2-1.2M., especially 0.5M.

A further embodiment of this invention is the preparation of compounds having the following formula:

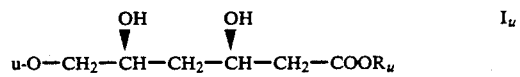

wherein
u is triphenylmethyl (i.e. "trityl"), and
$R_u$ is allyl or a radical, preferably $C_{1-3}$alkyl, n-butyl, i-butyl, t-butyl or benzyl,
by reduction according to this invention of the corresponding keto-hydroxy esters of the following formula:

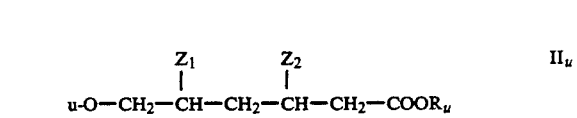

wherein $Z_1$ and $Z_2$ have the significances previously defined and where $R_u$ is as defined above.

Compounds $I_u$ are useful as intermediates in the preparation of aldehydes in chiral form which are useful in preparing corresponding final products I in chiral form. The use of such aldehydes in racemic form is disclosed in U.S. Pat. No. 4,571,428 (issued Feb. 18, 1986). The aforementioned multi-step process is disclosed in U.S. Pat. No. 4,870,199 (issued Sep. 26, 1989). Both the above-mentioned U.S. Patents are incorporated herein by reference.

Most of the above-recited molar amounts (ratios) are merely exemplary and may be varied, as is evident to one of ordinary skill in the art. For example, in a reaction of two compounds one of which is readily available and one of which is not, an excess of the readily available compound may be used to drive the reaction further towards completion (unless the use of an excess would increase the synthesis of an undesired compound).

Likewise, most of the above-indicated temperature ranges are merely exemplary, and it is within the ability of one of ordinary skill in the art to vary those that are not critical.

The reaction times set forth above are also merely exemplary and may be varied. As is well-known, the reaction time is often inversely related to the reaction temperature. Generally, each reaction is monitored by, for example, thin layer chromatography and is terminated when at least one starting material is no longer present, when it appears that no more of the desired product is being formed, etc.

It will also be understood that conventional work-up procedures may be employed.

The term "solvent", as utilized herein, embraces mixtures of solvents and implies that the reaction medium is a liquid at the desired reaction temperature. It should, therefore, be understood that not all of the solvents indicated for a particular reaction may be utilized for the entire recited temperature range. It should also be understood that the solvent must be at least substantially inert to the reactants employed, intermediates generated and end products under the reaction conditions utilized. Unless otherwise indicated, all solvent mixtures are by volume.

The term "inert atmosphere", means an atmosphere that does not react with any of the reactants intermediates or end products or otherwise interfere with the reaction. While a carbon dioxide atmosphere is suitable for certain reactions, the inert atmosphere is usually nitrogen, helium, neon, argon or krypton, or a mixture thereof, and most often nitrogen to maintain anhydrous conditions. Most reactions, including those where the use of an inert atmosphere is not specified, are carried out under an inert atmosphere, usually dry nitrogen or argon, for convenience.

The product may, if desired, be purified by conventional techniques such as recrystallization (if a solid), column chromatography (e.g., utilizing a silica gel column), preparative thin layer chromatography, gas chromatography (if sufficiently volatile), fractional distillation under high vacuum (if sufficiently volatile) or high pressure (performance) liquid chromatography (HPLC).

Throughout this specification, all temperatures are in degrees centigrade and room temperature (R.T.) is 20°–30° C., usually 20°–25° C., unless otherwise indicated, evaporations are done under vacuum employing minimal heating, drying of organic phases is done over anhydrous magnesium sulfate, and unless otherwise indicated, silica gel is utilized for all column chromatographies.

The following examples are illustrative of the invention.

EXAMPLE 1

Step A t-butyl
(±)-(E)-7-[3'-(4''-fluorophenyl)-1'-(1''-methylethyl)-1H-indol-2'-yl]-5-hydroxy-3-oxohept-6-enoate
(Compound i)

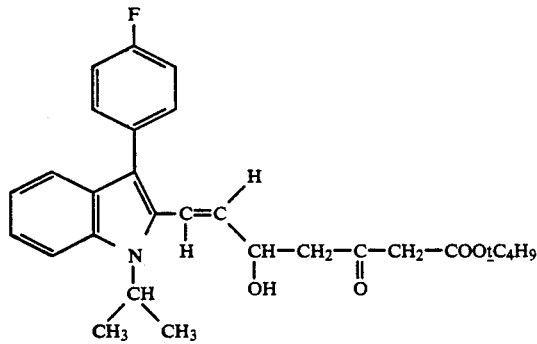

(a) To a suspension of 36 g. of sodium hydride (60% by weight in mineral oil) (0.9 moles) in 250 ml. of dry tetrahydrofuran at −10° C. is added 137 g. (0.866 mole) of t-butyl acetoacetate in 125 ml. of dry tetrahydrofuran, dropwise with stirring over a period of 40 minutes while maintaining an internal temperature of 0°–5° C. The reaction mixture is stirred at −10°–0° C. for 30 minutes and cooled to about −10° C. 541 ml. of 1.6M. n-butyllithium/n-hexane (0.866 mole) is added over about 40 minutes, the internal temperature of the reaction mixture being maintained at a temperature of about 0° C. The reaction mixture is stirred at −5°–0° C. for 20 minutes, and cooled to −10° C.

(b) A solution of 235 g. (0.749 mole) of 3-[3'-(4'-fluorophenyl)-1'-(1''-methethyl)-1H-indol-2'-yl]-2-propenal (prepared according to the processes disclosed in co-pending application Ser. No. 07/402,947, filed Sep. 5, 1989, which is hereby incorporated by reference) in 650 ml of dry tetrahydrofuran is added at a rate to maintain the internal temperature at −5°–0° C., over a period of about 40 minutes. The reaction mixture is stirred at 0°–5° C. under nitrogen for 20 minutes and cooled to −10° C.

(c) The reaction mixture is quenched with cold dilute hydrochloric acid (150 ml. concentrated HCl in 2 liters of water). To the resulting mixture is added 50 ml. of dry tetrahydrofuran, and the mixture is stirred vigorously for 15 minutes (until the pH of the aqueous layer is 3–4). The organic phase is separated and washed with a total of one liter of saturated sodium chloride solution (pH 5–6). The organic layer is concentrated at reduced pressure (about 25 mm) at 45°–50° C. until no further solvent distills. To the residual oil is added 200 ml. of toluene. The solvent is distilled and the crude residue is collected and used without further purification in the following step 1.

Step 1 t-butyl
(±)-erythro-(E)-7-[3'-(4''-fluorophenyl)-1'-(1''-methylethyl)indol-2'-yl]-3,5-dihydroxyhept-6-enoate
(Compound ii)

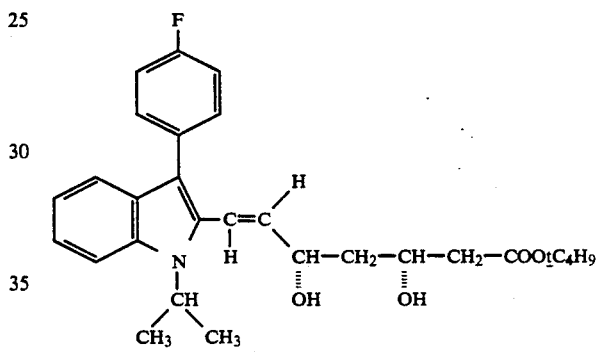

(a) 47.67 g. (1.26 moles) of sodium borohydride are added to a solvent comprising 1.32 liter of dry THF and 356 ml. of methanol under nitrogen at about −77° C. To the resulting solution is added 102 ml. of 50% (4.09 M)diethylmethoxyborane/THF over a 15 minute period, and the thus-formed mixture is stirred for an additional 10 minutes.

(b) 300.5 g. (0.464 mole) of 71.88% pure Compound i in 104 ml. THF and 26 ml. methanol at a temperature of about −74°–77° C. are added dropwise over to the mixture formed in (a) over a period of 1.5 hours, and the resulting mixture is stirred for an additional 30 minutes.

720 ml. saturated sodium bicarbonate solution and 1.75 liter heptane are added to quench the reaction. 500 ml. ethyl acetate is then added, and the resulting mixture is diluted with 3.5 liter of water with stirring for 15 minutes, the temperature of the mixture being about 10° C.

The top organic layer is separated and washed several times with a total of 2.4 liter of saturated sodium chloride solution, pH 7.5, and the organic layer is concentrated at 20–30 mm. Hg. at a maximum external temperature of about 45 ° C.

To the organic residue is added 375 ml. of toluene, and the solvent is distilled at 20–30 mm. Hg. at a maximum external temperature of about 45° C.

(c) 3.73 liter of ethyl acetate is added to the obtained thick oil (the cyclic boronate). 500 ml. of 30% hydrogen peroxide solution (4.41 moles) is then added to the ethyl acetate solution while maintaining an internal temperature of 25°–30° C. (the addition initially being exothermic), and the reaction mixture is stirred at 20°–25° C. for about 2 hours until thin layer chromatography shows no boronate present. (Alternatively in this step, aqueous sodium perborate solution may be used in place of the 30% hydrogen peroxide solution.)

The top organic layer is washed twice with a total of 2.22 liter of saturated sodium chloride solution, pH 7.5.

The top organic layer is then separated, washed three times with a total of 2.61 liters of 10% sodium sulfite solution (until the organic layer is free of peroxide) while maintaining an internal temperature of 25° C.

The top organic layer is then washed twice with a total of 1.72 liters of saturated sodium chloride solution, pH 7.5 and the solvent is distilled at 20–30 mm. Hg. and a maximum external temperature of about 45° C.

The residue is dissolved in 1.17 liter of refluxing ethyl acetate, the mixture is filtered while hot, and the filtrate is stirred at 20°–25° C. for 18 hours. The solids are collected by filtration, dried under reduced pressure (about 20–30 mm. Hg) at 25° C., washed with 550 ml. ethyl acetate/heptane (1:4) and redissolved in 880 ml. of ethyl acetate and stirred at ambient temperature for 18 hours. The solids are collected by filtration and washed with 480 ml. of ethyl acetate/heptane (1:2).

The solids are dried under reduced pressure to give a product of 114.5 g., m.p. 135°–137° C.

A second crop is obtained from the mother liquors, to give a total yield of 149.5 g.

The product has a chemical purity of 99.44%, and is 99.67% pure erythro isomer. It may be resolved into two optically active enantiomers, the 3R, 5S and 3S,5R, of which the former is preferred.

Alternate Step 1

(a) 22 g. (0.566 mole) of sodium borohydride powder are added over a period of about 10 minutes to a solvent comprising 1.216 liter of dry THF and 330 ml. of methanol under nitrogen at about −77° C., and the resulting solution is stirred for 15 minutes. To this solution is added 79.3 ml. of 50 wt.% diethylmethoxyborane/THF (containing 64.9 g (0.325 mole) of diethylmethoxyborane) over a 15 minute period so that the internal temperature does not exceed −74° C., and the thus-formed mixture is stirred for an additional 10 minutes.

(b) A solution of 301.4 g. (0.464 mole) of 78.6% pure Compound i in 208 ml. THF and 52 ml. methanol is added dropwise to the mixture formed in (a) over a period of 1.25 hours while maintaining an internal temperature of about −74°–−76° C., and the resulting mixture is stirred for an additional 45 minutes.

The above reaction mixture is quenched by a solution comprising 720 ml. saturated sodium bicarbonate solution, 400 ml. ethyl acetate and 1.2 liter of water. 400 ml. of ethyl acetate is then added, and the resulting mixture is allowed to warm to 15° C. over a period of 15 minutes.

The top organic layer is separated and washed twice with a total of 1.6 liter of saturated sodium chloride solution, pH 5–6, and the organic layer is concentrated at 20–30 mm. Hg. at a maximum external temperature of about 50°–60° C. to dryness.

To the residue is added in three portions a total of 300 ml. ethyl acetate, and the solvent is distilled at 20–30 mm. Hg. at a maximum external temperature of about 50°–60° C.

(c) 3.73 liter of ethyl acetate at 25°–30° C. is added to the obtained thick oil (the cyclic boronate), and the resulting brown solution is cooled to 20° C. 500 ml. of 30% hydrogen peroxide solution (4.41 moles) is then added over 20 minutes while maintaining an internal temperature of 25°–30° C. (the addition initially being exothermic), and the reaction mixture is stirred at 26°–28° C. for about 3 hours until thin layer chromatography shows no boronate present.

The top organic layer is washed twice with a total of 2 liters of saturated sodium chloride solution, pH 5–6.

The top organic layer is then separated and washed twice with a total of 2 liters of 10% sodium sulfite solution, pH 9–10, (until the organic layer is free of peroxide).

The top organic layer is washed with 1 liter of saturated sodium bicarbonate solution and then with 1.2 liters of deionized water. The solvent is distilled from the organic layer at 20–30 mm. Hg. and a maximum external temperature of about 50–60° C. until no further solvent distills.

The residue is dissolved in 150 ml. of ethyl acetate and 1.35 liter of heptane, and the mixture is heated to 48–50° C. with stirring for 30 minutes. The mixture is then cooled to 20° C. and maintained at 20° C. for 30 minutes, with vigorous stirring. The solids are collected by filtration, washed twice with a total of 200 ml. of ethyl acetate/heptane (1:9), and dried under reduced pressure (about 20–30 mm. Hg) at 20° C. for 2 hours.

The solids are then redissolved in 900 ml. of ethyl acetate, and the mixture is heated to refluxing temperatures (65°–70° C.) until a light brown homogeneous solution is obtained. The solution is cooled to −3°–−5° C. over a period of one hour, at which temperature it is maintained for 30 minutes. The solids are collected by filtration and washed twice with a total of 240 ml. of ethyl acetate at −5°–−10° C.

The solids are dried at 60°–65° C. under reduced pressure over about 2 days to give a product of 162.3 g., m.p. 139°–140° C.

The product has a chemical purity of 98.56%, and is 99.45% pure erythro isomer.

A second crop of 9.3 g. is obtained from the combined filtrate and washings, having a purity of 91.06%, of which 97.22% is the pure erythro isomer.

The following steps may optionally be taken to improve product purity, increase stereoselectivity and/or decrease boron content of the product:

(i) If the purity of the product is less than 98%, the erythro/threo ratio is less than 99/1, and/or the boron content is more than 10 ppm, it is desirable to repeat either or both of steps (d) and (e) above.

(ii) If the boron content of the product is greater than 10 ppm (and the erythro/threo ratio is greater than 99/1, and the purity is greater than 98%) then the reaction mixture in step (c) can be stirred for a longer period of time (e.g., (4–5 hours); and as a final step in step (e), the solids may be washed with deionized water.

(iii) If the erythro/threo ratio is less than 99/1, and purity is less than 98% (and boron content is less than 10 ppm), then in step(a), a quantity of about 10–20% additional diethylmethoxyborane (50% in THF) may be employed; and in step (e), about 10% more ethyl acetate may be employed.

(iv) If the product contains boron in an amount greater than 10 ppm and the erythro/threo ratio is less than 99/1, and purity is less than 98%, steps (i)–(iii) above may be employed.

Step B

Sodium (E)-(±)-7-[3′(4″fluorophenyl)-1′(1″-methylethyl)-1H-indol-2′-yl]-3,5-dihydroxy-6-hept-6-enoate

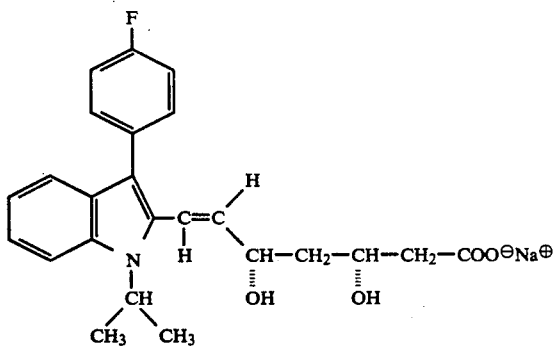

To mixture of 35.0 g. (75 mmole) of Compound ii, and 175 ml. of 95% ethanol under nitrogen is added 74 ml. of 1N sodium hydroxide solution (74 mmoles) while maintaining the internal temperature below about 15° C. Borosilicate-free glassware is used throughout. The suspension is stirred at 30°-35° C. for one hour, until the pH is 7-8. The solvent is evaporated at reduced pressure at 45° C., and the residue is dissolved in 250 ml. of water. The distillation is continued until the remaining volume is about 115 ml. 315 ml. of deionized water are added, and the solution is gently washed in three portions with a total of 525 ml. of t-butyl methyl ether. The solution is concentrated at reduced pressure to about 245 ml., to which 185 ml. of deionized water is added. The aqueous solution is lyophilized to obtain the product (29.75 g.), m.p. 210°-225° C. (dec.).

N.M.R. (CD$_3$OD) 1.40-1.78 (2H, multiplet); 1.62 (6H, doublet); 2.20-2.42 (2H, multiplet); 3.96 (1H, multiplet); 4.38 (1H, multiplet); 4.90 (1H, multiplet); 5.72 (1H, doublet of a doublet); 6.70 (1H, doublet); 6.96-7.55 (8H, multiplet).

EXAMPLE 2

Methyl (±)-erythro-(E)-7-[3′-(4″-fluorophenyl)-1′-(1″-methylethyl)-1H-indol-2′-yl]-3,5-dihydroxy-hept-6-enoate

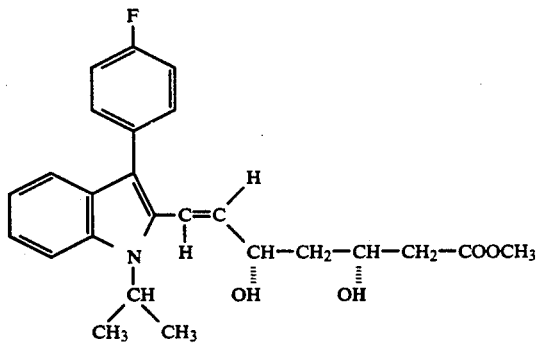

(a) 12.9 g. (0.341 moles) of sodium borohydride are added to a solvent comprising 2.28 liter of dry THF and 644 ml. of methanol under nitrogen at about −78° C. To the resulting solution is added 298 ml. of 15% diethylmethoxyborane/ THF over a 25 minute period, and the thus-formed mixture is stirred for an additional 5 minutes.

(b) 118.5 g. (0 28 mole) of methyl(±)(E)-[7-(3′-(4″-fluorophenyl)-1′- (1″-methylethyl)indol-2′-yl]-5-hydroxy-3-oxohept-6-enoate in 3.8 liters of THF and 95 ml. methanol at about −76°-−77° C. in 104 ml. THF and 26 ml. methanol at a temperature of about −74°-77° C. are added dropwise to the mixture formed in (a) over a period of 2 hours, with stirring for an additional 2 hours.

425 ml. of saturated ammonium chloride solution is then added to quench the reaction, the internal temperature being maintained at about −65° C. 1.185 liter of ethylacetate is then added, and the resulting mixture is diluted with 1.42 liter of water and 1.185 liter of heptane, the resulting temperature of the mixture being about 5° C.

The top organic layer is separated and washed several times with a total of 1.4 liter of saturated sodium chloride solution, and the solvent is distilled at 20-30 mm. Hg. at a maximum external temperature of about 45° C. 150 ml. of ethyl acetate is then added to the residue, and the solvent is distilled at 20-30 mm. Hg. at a maximum external temperature of about 45° C.

(c) To the organic residue (the cyclic boronate) is added 2.375 liter of ethyl acetate. 264 ml. of 30% hydrogen peroxide solution (2.328 moles) is then slowly added so as to maintain an internal temperature of 20°-25° C. (the addition initially being exothermic), and the reaction mixture is stirred at 20°-25° C. for about 2 hours until thin layer chromatography shows no boronate present.

The top organic layer is washed twice with a total of 1.2 liter of saturated sodium chloride solution, pH 7.5.

The top organic layer is then separated, washed three times (for ten minutes each time) with a total of 1.32 liter of cold (0°-5° C.) 10% sodium sulfite solution (until the organic layer is free of peroxide) while maintaining an internal temperature of 25° C. and the organic layer is washed successively with a total of 350 ml of saturated sodium chloride solution (pH 7.5).

The solvent is distilled at 20-30 mm. Hg. and a maximum external temperature of about 45° C.

The residue is then dissolved in 130 ml. isopropanol. The mixture is heated to refluxing temperature.

While hot, 14 g. of boric acid are added and refluxing is continued for 15 minutes. The mixture is then filtered and the filtrate is stirred at 20°-25° C. for 18 hours. The solids are collected by filtration, washed with 100 ml. of isopropanol, and dried under reduced pressure to give a product of 110 g. (80% yield). The product is redissolved in methanol and recrystallized, and the melting point is taken, 124°-126° C.

The product is 99.07% pure erythro racemate, which may be resolved into two optical enantiomers, the 3R,5S and 3S,5R, of which the former is preferred.

EXAMPLE 3 t-butyl (+)-erythro-(E)-3,5-dihydroxy-7-[1'-(4''-fluorophenyl)-4'-(1''-methylethyl)-2'-phenyl-1H-imidazol-5'-yl]-hept-6-enoate

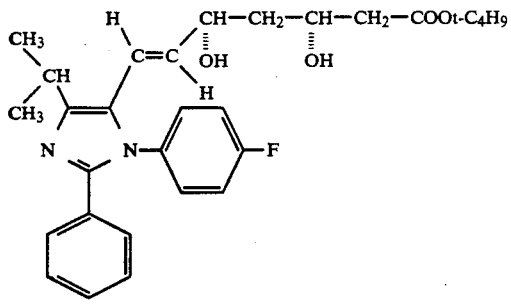

(a) 10 27 g. (0.27 mole) of sodium borohydride are added to a solvent comprising 1.67 liter of dry THF and 513 ml. of methanol under nitrogen at about −76° C. To the resulting solution is added 387 ml. of 15% diethylmethoxyborane/ THF over a 30 minute period, while maintaining the internal temperature below −77.5° C., and the thus-formed mixture is stirred for an additional 5 minutes.

(b) 110 g. (0.223 mole) of t-butyl (+)-(E)-7-[1'-(4''-fluorophenyl)-4'-(1-methylethyl)-2'-phenyl-1H-imidazol-5'-yl]-5-hydroxy-3-oxohept-6-enoate in 304 ml. THF and 76 ml. methanol at a temperature of about −74°-−77° C. are added dropwise to the mixture formed in (a) over a period of two hours. The resulting yellow solution is stirred at −76.5° C. for six hours.

425 ml. saturated ammonium chloride is then added to quench the reaction, the temperature being maintained at about −65° C. 950 ml. of ethyl acetate, 950 ml. of hexane and 1.13 liter of water are added, the temperature of the mixture being about 5° C. and the mixture is stirred for 15 minutes, the resulting temperature of the mixture being about 5° C.

The top organic layer is separated and washed successively with a total of 1.4 liter saturated sodium chloride solution (pH 7.5), and the solvent is distilled at 20–30 mm. Hg. at a maximum external temperature of about 45° C.

(c) 3.25 liter of ethyl acetate is added to the obtained oil (the cyclic boronate). 340 ml. of 30% hydrogen peroxide solution (3 moles) is then slowly added so as to maintain an internal temperature of 20°-25° C., and the reaction mixture is stirred at 20°-25° C. for about 3 hours until thin layer chromatography shows no boronate present.

The top organic layer is washed twice with a total of 1.6 liter of saturated sodium chloride solution, pH 7.5.

The top organic layer is then separated, washed three times (for ten minutes each time ) with a total of 1.74 liters of 10% sodium sulfite solution (until the organic layer is free of peroxide) while maintaining an internal temperature of 25° C.

The top organic layer is washed with 600 ml of saturated sodium chloride solution (pH 7.5).

The solvent is distilled at 20–30 mm. Hg. at a maximum external temperature of about 45° C.

106 g. of crude material is obtained.

Purification of 0.68 g. of the crude dihydroxy ester is done by column chromatography using ethyl acetate/hexane (1:2) as the eluant, yielding 490 mg., m.p. 143°-145° C., which is shown by NMR analysis to contain the erythro isomer in 98.78% purity (there being no threo isomer present), $[\alpha]_D = +6.49°$ (C=0.77, $CH_2Cl_2$).

EXAMPLE 4 t-butyl(−)erythro-dihydroxy-6-trityloxyhexanoate

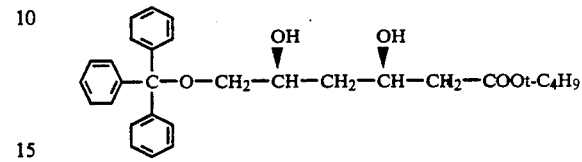

(a) 5.61 g. (148.4 mmoles) of sodium borohydride are added to a solvent comprising 990 ml. of dry THF and 280 ml. of methanol under nitrogen at about −76° C. The temperature increases to about −74° C. To the resulting solution is added 129.7 ml. of 15% diethylmethoxyborane/THF dropwise over a 20 minute period, and the thus-formed mixture is stirred for an additional 10 minutes at −77° to −76° C.

(b) 56 g. (0.122 mmole) of t-butyl 5S-hydroxy-6-trityloxy-3-oxo-hexanoate in 165 ml. THF and 41 ml. methanol at a temperature of about −77°-−75° C. are added dropwise to the mixture formed in (a) over a period of 40 minutes, and the resulting mixture is stirred for an additional two hours at −77°-−75° C.

156 ml. saturated ammonium chloride solution is added to quench the reaction. 500 ml. of ethyl acetate, 500 ml. of heptane and 600 ml. of water are then added.

The top organic layer is separated and washed successively with a total of 600 ml. of saturated sodium chloride solution, pH 7.5, and the organic layer is concentrated at 20-30 mm. Hg. at a maximum external temperature of about 45° C.

(c) 793 ml. of ethyl acetate is added to the obtained organic residue (containing predominantly the cyclic boronate). 79 ml. of 30% hydrogen peroxide solution (0.7 moles) is then slowly added, and the reaction mixture is stirred for about 3 hours until thin layer chromatography shows no boronate present.

The top organic layer is washed twice with a total of 400 ml. of saturated sodium chloride solution, pH 7.5.

The top organic layer is then separated, washed three times (for ten minutes each time) with a total of 576 ml. of 10% sodium sulfite solution (until the organic layer is free of peroxide) while maintaining an internal temperature of 25° C.

The top organic layer is then washed successively with a total of 200 ml. of saturated sodium chloride solution, pH 7.5, and the solvent is distilled at 20-30 mm. Hg. and a maximum external temperature of about 45° C.

54.3 g. of the crude dihydroxy compound are obtained, which contains 99.19% erythro isomer, [m.p. 84°-86° C.], $[\alpha]_D^{20} = -5.59$ (c=1.6, $CH_2Cl_2$).

What is claimed is:

1. A process for synthesizing compounds of the formula:

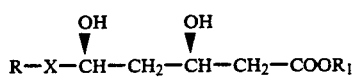

I

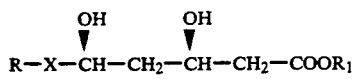

$$\text{R—X—CH—CH}_2\text{—CH—CH}_2\text{—COOR}_1 \quad \text{I}$$

from compounds of the formula:

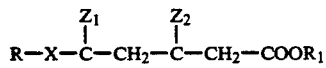

$$\text{R—X—C—CH}_2\text{—C—CH}_2\text{—COOR}_1 \quad \text{II}$$

wherein
X is —CH$_2$—CH$_2$— or —CH=CH—,
Z$_1$ and Z$_2$ are either =O or

provided that Z$_1$ and Z$_2$ are not the same,
R$_1$ is an ester group inert to the reaction conditions, and
R is an organic radical having groups which are inert under reducing conditions, comprising:
a. providing a reaction medium comprising sodium borohydride in about 3 to 6 parts of tetrahydrofuran to 1 part by volume of an allyl alcohol or lower alcohol having 1 to 4 carbon atoms; and an effective amount of a compound of Formula III:

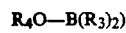

R$_4$O—B(R$_3$)$_2$)  III wherein R$_3$ is a primary or secondary alkyl having from 2 to 4 carbon atoms; and R$_4$ is allyl or alkyl having from 1 to 4 carbon atoms;
b. treating a compound of Formula II with said reaction medium under conditions suitable for formation of a cyclic boronate ester and/or boron complex of a compound of Formula I, wherein said cyclic boronate ester is formed; and
c. cleaving the product of step (b) to obtain the corresponding compound of Formula I.

2. The process of claim 1 wherein R is a group of Formula A, B, C, D, Ea, Eb, Ec, F, G, H, J, K, L, M, and N, i.e. as follows:

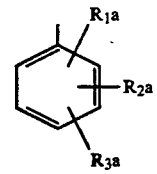

wherein
each of R$_{1a}$, R$_{2a}$ and R$_{3a}$ is independently hydrogen; halo; C$_{1-4}$alkyl, C$_{1-4}$haloalkyl, phenyl, phenyl substituted by halo, C$_{1-4}$alkoxy, C$_{2-8}$alkanoyloxy, C$_{1-4}$alkyl or C$_{1-4}$haloalkyl, or —OR$_{4a}$ in which R$_{4a}$ is hydrogen, C$_{2-8}$alkanoyl, benzoyl, phenyl, halophenyl, phenyl(C$_{1-3}$alkyl), C$_{1-9}$alkyl, cinnamyl, C$_{1-4}$haloalkyl, allyl, cycloalkyl(C$_{1-3}$alkyl), adamantyl(C$_{1-3}$alkyl) or substituted phenyl (C$_{1-3}$alkyl) each substituent of which is selected from the group consisting of halo, C$_{1-4}$alkoxy, C$_{1-4}$alkyl and C$_{1-4}$haloalkyl;

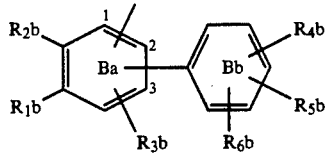

wherein R$_{1b}$ and R$_{2b}$ together form a radical of the formula:

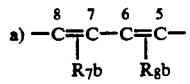

or b) —CH$_2$—CH$_2$—CH$_2$—CH$_2$—, wherein
R$_{3b}$ is hydrogen, C$_{1-3}$alkyl, C$_{1-3}$alkoxy, trifluoromethyl, fluoro, chloro, phenoxy or benzyloxy,
R$_{4b}$ is hydrogen, C$_{1-3}$alkyl, n-butyl, i-butyl, C$_{1-3}$alkoxy, n-butoxy, i-butoxy, trifluoromethyl, fluoro, chloro, phenoxy or benzyloxy,
R$_{5b}$ is hydrogen, C$_{1-3}$alkyl, C$_{1-3}$alkoxy, trifluoromethyl, fluoro, chloro, phenoxy or benzyloxy,
with the provisos that not more than one of R$_{4b}$ and R$_{5b}$ is trifluoromethyl, not more than one of R$_{4b}$ and R$_{5b}$ is phenoxy, and not more than one of R$_{4b}$ and R$_{5b}$ is benzyloxy; and
R$_{6b}$ is hydrogen, C$_{1-2}$alkyl, C$_{1-2}$alkoxy, fluoro or chloro;
R$_{7b}$ is hydrogen, C$_{1-3}$alkyl, n-butyl, i-butyl, C$_{1-3}$alkoxy, n-butoxy, i-butoxy, trifluoromethyl, fluoro, chloro, phenoxy or benzyloxy;
R$_{8b}$ is hydrogen, C$_{1-3}$alkyl, C$_{1-3}$alkoxy, trifluoromethyl, fluoro, chloro, phenoxy or benzyloxy;
with the provisos that not more than one of R$_{7b}$ and R$_{8b}$ is trifluoromethyl, not more than one of R$_{7b}$ and R$_{8b}$ is phenoxy, and not more than one of R$_{7b}$ and R$_{8b}$ is benzyloxy;
with the proviso that the free valence on ring Ba and ring Bb are ortho to each other;

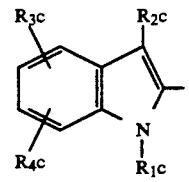

wherein one of R$_{1c}$ and R$_{2c}$ is phenyl substituted by R$_{5c}$, R$_{6c}$ and R$_{7c}$ and the other is C$_{1-3}$alkyl, n-butyl or i-butyl,
R$_{3c}$ is hydrogen, C$_{1-3}$alkyl, n-butyl, i-butyl, t-butyl, C$_{1-3}$alkoxy, n-butoxy, i-butoxy, trifluoromethyl, fluoro, chloro, phenoxy or benzyloxy,
R$_{4c}$ is hydrogen, C$_{1-3}$alkyl, C$_{1-3}$alkoxy, trifluoromethyl, fluoro, chloro, phenoxy or benzyloxy,
with the provisos that not more than one of R$_{3c}$ and R$_{4c}$ is trifluoromethyl, not more than one of R$_{3c}$ and R$_{4c}$ is phenoxy, and not more than one of R$_{3c}$ and R$_{4c}$ is benzyloxy, $R_{5c}$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_{6c}$ is hydrogen, $C_{1-3}$alkyl, $C_{1-3}$alkoxy, trifluoromethyl, fluoro, chloro, phenoxy or benzyloxy, with the provisos that not more than one of $R_{5c}$ and $R_{6c}$ is trifluoromethyl, not more than one of $R_{5c}$ and $R_{6c}$ is phenoxy, and not more than one of $R_{5c}$ and $R_{6c}$ is benzyloxy, and $R_{7c}$ is hydrogen, $C_{1-2}$alkyl, $C_{1-2}$alkoxy, fluoro or chloro;

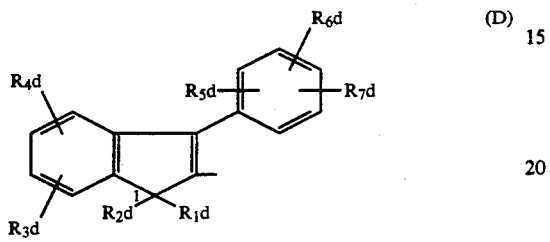

(D)

wherein $R_{1d}$ is hydrogen or primary or secondary $C_{1-6}$alkyl not containing an asymmetric carbon atom, and $R_{2d}$ is primary or secondary $C_{1-6}$alkyl not containing an asymmetric carbon atom or $R_{1d}$ and $R_{2d}$ taken together are —$(CH_2)_m$— or —(Z)—$CH_2$—$CH$=$CH$—$CH_2$—, wherein m is 2,3,4,5,or 6;

$R_{3d}$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_{4d}$ is hydrogen, $C_{1-3}$alkyl, $C_{1-3}$alkoxy, trifluoromethyl, fluoro, chloro, phenoxy or benzyloxy, with the provisos that not more than one of $R_{2d}$ and $R_{3d}$ is trifluoromethyl, not more than one of $R_{2d}$ and $R_{3d}$ is phenoxy, and not more than one of $R_{2d}$ and $R_{3d}$ is benzyloxy, $R_{5d}$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy, $R_{6d}$ is hydrogen, $C_{1-3}$alkyl, $C_{1-3}$alkoxy, trifluoromethyl, fluoro, chloro, phenoxy or benzyloxy, with the provisos that not more than one of $R_{5d}$ and $R_{6d}$ is trifluoromethyl, not more than one of $R_{5d}$ and $R_{6d}$ is phenoxy, and not more than one of $R_{5d}$ and $R_{6d}$ is benzyloxy, $R_{7d}$ is hydrogen, $C_{1-2}$alkyl, $C_{1-2}$alkoxy, fluoro or chloro;

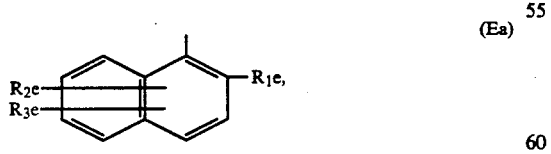

(Ea)

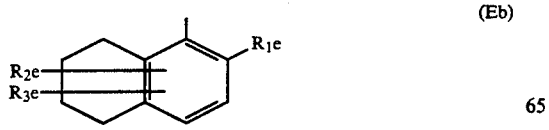

(Eb)

or

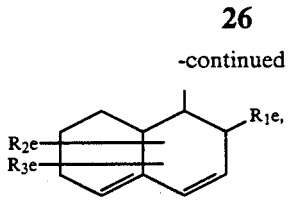

(Ec)

wherein each of $R_1e$, $R_2e$ and $R_3e$ is independently fluoro, chloro, hydrogen or $C_{1-4}$alkyl, $R_1e$ preferably being methyl;

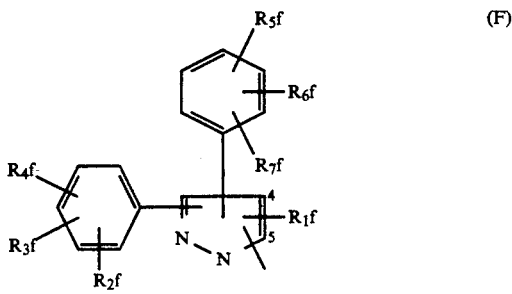

(F)

wherein $R_1f$ is $C_{1-6}$alkyl not containing an asymmetric carbon atom, each of $R_2f$ and $R_5f$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, phenyl, phenoxy or benzyloxy, each of $R_3f$ and $R_6f$ is independently hydrogen, $C_{1-3}$alkyl, $C_{1-3}$alkoxy, trifluoromethyl, fluoro, chloro, phenoxy or benzyloxy, and each of $R_4f$ and $R_7f$ is independently hydrogen, $C_{1-2}$alkyl, $C_{1-2}$alkoxy, fluoro or chloro, with the provisos that not more than one of $R_2f$ and $R_3f$ is trifluoromethyl, not more than one of $R_2f$ and $R_3f$ is phenoxy, not more than of $R_2f$ and $R_3f$ is benzyloxy, not more than one of $R_5f$ and $R_6f$ is trifluoromethyl, not more than one of $R_5f$ and $R_6f$ is phenoxy, and not more than one of $R_5f$ and $R_6f$ is benzyloxy;

with the provisos that (i) the free valence of the pyrazole ring is in the 4- or 5- position, and (ii) the $R_1f$ group and the free valence are ortho to each other;

(G)

wherein

Rag is a single bond to X, Rbg is $R_2g$, Rcg is $R_3g$, Rdg is $R_4g$, and Yg is

or

Rag is $R_1g$, Rbg is a single bond to X, Rcg is $R_2g$, Rdg is $R_3g$, and Yg is O, S or

$R_{1g}$, $R_{2g}$, $R_{3g}$ and $R_{4g}$ independently are $C_{1-6}$alkyl not containing an asymmetric carbon atom, $C_{3-7}$-cycloalkyl or phenyl substituted by $R_{5g}$, $R_{6g}$ and $R_{7g}$; or in the case of $R_{3g}$ and $R_{4g}$ additionally hydrogen, or for $R_{3g}$ when $Y_g$ is O or S, and X is X', additionally Ga where Ga is as follows:

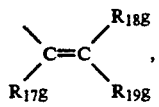 (Ga)

wherein
$R_{17g}$ is hydrogen or $C_{1-3}$alkyl,
and $R_{18g}$ and $R_{19g}$ are independently hydrogen, $C_{1-3}$alkyl or phenyl,
each $R_{5g}$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy or benzyloxy,
each $R_{6g}$ is independently hydrogen, $C_{1-3}$alkyl, $C_{1-3}$alkoxy, trifluoromethyl, fluoro, chloro, bromo, phenoxy or benzyloxy, and
each $R_{7g}$ is independently hydrogen, $C_{1-2}$alkyl, $C_{1-2}$alkoxy, fluoro or chloro,
with the proviso that there may only be one each of trifluoromethyl, phenoxy and benzyloxy on each phenyl ring substituted by $R_{5g}$, $R_{6g}$, and $R_{7g}$;

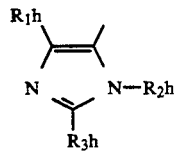 (H)

wherein
$R_{1h}$ is $C_{1-6}$alkyl not containing an asymmetric carbon atom, $C_{3-7}$cycloalkyl, adamantyl-1 or phenyl substituted by $R_{4h}$, $R_{5h}$ and $R_{6h}$,
$R_{2h}$ is $C_{1-6}$alkyl not containing an asymmetric carbon atom, $C_{3-7}$cycloalkyl, adamantyl-1 or phenyl substituted by $R_{7h}$, $R_{8h}$ and $R_{9h}$,
$R_{3h}$ is hydrogen, $C_{1-6}$ alkyl not containing an asymmetric carbon atom, $C_{3-7}$cycloalkyl, adamantyl-1, styryl or phrnyl substituted by $R_{10h}$, $R_{11h}$ and $R_{12h}$,
wherein each of $R_{4h}$, $R_{7h}$ and $R_{10h}$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy, or benzyloxy,
each of $R_{5h}$, $R_{8h}$ and $R_{11h}$ is independently hydrogen, $C_{1-3}$alkyl, $C_{1-3}$alkoxy, trifluoromethyl, fluoro, chloro, bromo, —COOR$_{17h}$, —N(R$_{19h}$)$_2$, phenoxy or benzyloxy, wherein $R_{17h}$ is hydrogen, $R_{18h}$ or M, wherein $R_{18h}$ is $C_{1-3}$alkyl, n-butyl, i-butyl, t-butyl or benzyl, and M is as defined above, and each $R_{19h}$ is independently $C_{1-6}$alkyl not containing an asymmetric carbon atom, and
each of $R_{6h}$, $R_{9h}$ and $R_{12h}$ is independently hydrogen, $C_{1-2}$alkyl, $C_{1-2}$alkoxy, fluoro or chloro, with the provisos that not more than one substituent on each of Rings Ha, Hb and Hc independently is trifluoromethyl, not more than one substituent on each of Rings Ha, Hb and Hc independently is phenoxy, and not more than one substituent on each of Rings Ha, Hb and Hc independently is benzyloxy,

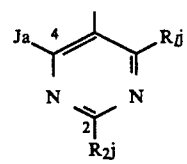 (J)

wherein
each of $R_{1j}$ and $R_{2j}$ is, independently $C_{1-6}$alkyl not containing an asymmetric carbon atom, $C_{3-6}$cycloalkyl or phenyl—(CH$_2$)$_m$—, wherein m is 0, 1, 2 or 3, and the phenyl group is unsubstituted or substituted by any of $R_{3j}$, $R_{4j}$ and $R_{5j}$ wherein $R_{3j}$-$R_{5j}$ are as defined below; or

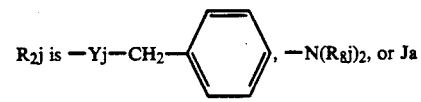

wherein
$Y_j$ is —O— or —S—;
each $R_{8j}$ is independently $C_{1-4}$alkyl not containing an asymmetric carbon atom, or may form part of a 5, 6, or 7 membered ring Jb, said Ring Jb being substituted or unsubstituted and optionally also containing one or more hetero-atoms; and
Ja is Ja' or Ja" where Ja' is a heterocyclic group which is unsubstituted or substituted by one or two $C_{1-2}$alkyl or $C_{1-2}$alkoxy groups; and Ja" is Ja"a or Ja"b

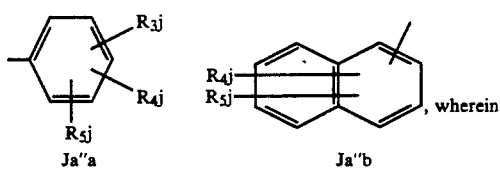

$R_{3j}$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy, or benzyloxy,
$R_{4j}$ is hydrogen, $C_{1-3}$alkyl, $C_{1-3}$alkoxy, trifluoromethyl, fluoro, chloro, phenoxy or benzyloxy, and
$R_{5j}$ is hydrogen, $C_{1-2}$alkyl, $C_{1-3}$alkoxy, fluoro or chloro;
the provisos that not more than one of $R_{3j}$ and $R_{4j}$ is trifluoromethyl, not more than one of $R_{3j}$ and $R_{4j}$ is phenoxy, and not more than one of $R_{3j}$ and $R_{4j}$ is benzyloxy;

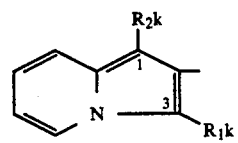 (K)

wherein each of $R_1k$ and $R_2k$ is independently
(a) phenyl substituted by $R_5k$, $R_6k$ and $R_7k$,
(b) hydrogen or a primary or secondary $C_{1-6}$alkyl not containing an asymmetric carbon atom;
(c) $C_{3-6}$cycloalkyl; or
(d) phenyl—$(CH_2)_m$—, wherein m is 1, 2 or 3, wherein
$R_5k$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy;
$R_6k$ is hydrogen, $C_{1-3}$alkyl, $C_{1-3}$alkoxy, fluoro, or chloro; and
$R_7k$ is hydrogen, $C_{1-2}$alkyl, $C_{1-2}$alkoxy, fluoro or chloro.

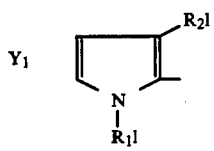

(L)

wherein
$Y_1$ is —CH=CH—CH=N—, —C=CH—N=CH—, —CH=N—CH=CH— or —N=CH—CH=CH—
$R_1l$ is primary $C_{1-6}$alkyl not containing an asymmetric carbon atom; or isopropyl;
$R_2l$ is
(a) phenyl substituted by $R_5l$, $R_6l$ and $R_7l$,
(b) a primary or secondary $C_{1-6}$alkyl not containing an asymmetric carbon atom,
(c) $C_{3-6}$cycloalkyl or
(d) phenyl—$(CH_2)_m$—, wherein
$R_5l$ is t-butyl, $C_{1-3}$alkoxy, n-butoxy, i-butoxy, trifluoromethyl, fluoro, chloro, phenoxy or benzyloxy;
$R_6l$ is hydrogen, $C_{1-3}$alkyl, $C_{1-3}$alkoxy, trifluoromethyl, fluoro, chloro, phenoxy or benzyloxy;
with the provisos that not more than one of $R_5l$ and $R_6l$ is trifluoromethyl, not more than one of $R_5l$ and $R_6l$ is phenoxy, and not more than one of $R_5l$ and $R_6l$ is benzyloxy,
$R_7l$ is hydrogen, $C_{1-2}$alkyl, $C_{1-2}$alkoxy, fluoro or chloro, and
m is 1, 2 or 3;

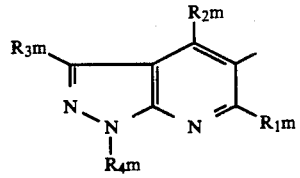

(M)

wherein
$R_1m$ is $C_{1-6}$alkyl not containing an asymmetric carbon atom, $C_{5-7}$cycloalkyl, $(C_{5-7}$cycloalkyl)methyl, phenyl—$(CH_2)_m$—, pyridyl-2, pyridyl-3, pyridyl-4, thienyl-2, thienyl-3 or phenyl substituted by $R_5m$, $R_6m$ and $R_7m$,
$R_2m$ is $C_{1-6}$alkyl not containing an asymmetric carbon atom, $C_{5-7}$cycloalkyl, $(C_{5-7}$cycloalkyl)methyl, phenyl—$(CH_2)_m$—, pyridyl-2, pyridyl-3, pyridyl-4, thienyl-2, thienyl-3 or phenyl substituted by $R_8m$, $R_9m$ and $R_{10}m$,
with the proviso that not more than one of $R_1m$ and $R_2m$ is a member of the group consisting of pyridyl-2, pyridyl-3, pyridyl-4, thienyl-2, thienyl-3, phenyl substituted by $R_5m$, $R_6m$ and $R_7m$, and phenyl substituted by $R_8m$, $R_9m$ and $R_{10}m$,
$R_3m$ is $C_{1-6}$alkyl not containing an asymmetric carbon atom, $C_{5-7}$cycloalkyl or phenyl substituted by $R_{11}m$, $R_{12}m$ and $R_{13}m$,
$R_4m$ is $C_{1-6}$alkyl not containing an asymmetric carbon atom, $C_{5-7}$cycloalkyl or phenyl substituted by $R_{14}m$, $R_{15}m$ and $R_{16}m$,
wherein
each of $R_5m$, $R_8m$, $R_{11}m$ and $R_{14}m$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, bromo, phenyl, phenoxy or benzyloxy,
each of $R_6m$, $R_9m$, $R_{12}m$ and $R_{15}m$ is independently hydrogen, $C_{1-3}$alkyl, $C_{1-3}$alkoxy, trifluoromethyl, fluoro, chloro, phenoxy or benzyloxy, and
each of $R_7m$, $R_{10}m$, $R_{13}m$ and $R_{16}m$ is independently hydrogen, $C_{1-2}$alkyl, $C_{1-2}$alkoxy, fluoro or chloro,
with the provisos that not more than one substituent on each phenyl ring independently is trifluoromethyl, not more than one substituent on each phenyl ring independently is phenoxy, and not more than one substituent on each phenyl ring independently is benzyloxy.

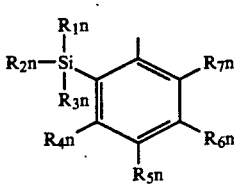

[N]

wherein
each of $R_1n$, $R_2n$ and $R_3n$ is independently alkyl having from 1 to 4 carbon atoms; or phenyl which may be unsubstituted or substituted either by one or two alkyl or alkoxy groups having from 1 to 3 carbon atoms, or chloro, or by one fluoro, bromo or trifluoromethyl substituent;
$R_4n$ is a hydrogen atom or alkyl having from 1 to 3 carbon atoms, e.g., methyl;
$R_5n$ is a hydrogen atom; lower alkyl or alkoxy, halo, trifluoromethyl; or phenyl, benzyl, or benzyloxy, wherein the aromatic portion may be unsubstituted or substituted by up to two groups, one of which may be fluoro, bromo or trifluoromethyl; or one or two of which may be lower alkyl, alkoxy or chloro;
$R_6n$ is a hydrogen atom, lower alkyl or alkoxy, halo, or trifluoromethyl; and
$R_7n$ is a hydrogen atom, lower alkyl or alkoxy, halo or trifluoromethyl;
and any of $R_6n+R_7n$, $R_5n+R_6n$, or $R_6n+R_7n$ may constitute a 4 carbon radical, which is either —CH=CH—CH=CH— or —$(CH_2)_4$—, to form a ring which is substituted by $R_8n$ which is hydrogen, halo, lower alkyl or alkoxy;
provided that there be no more than one trifluoromethyl group, and no more than two bromo substituents present on the molecule.

3. The process of claim 1 wherein the compound of Formula III is prepared by reacting a trialkylborane of formula V:

$B(R_3)_3$     V in which R₃ is as defined, under essentially anhydrous conditions, with an alcohol of formula VI:

R₄OH      VI in which R₄ is as defined.

4. The process of claim 1 in which R₃ is ethyl and R₄ is methyl.

5. The process of claim 1 which is carried out in a reaction medium consisting essentially of from 3 to 6 parts of tetrahydrofuran per part by volume of an alcohol.

6. The process of claim 1 wherein steps a and b are carried out in inert atmosphere.

7. The process of claim 1, wherein the molar ratio of sodium borohydride to the compound of Formula II is about 1.1:1 to 1.5:1.

8. The process of claim 1, wherein the molar ratio of of the compound of Formula III to the compound of Formula II is at least about 0.5:1.

9. The process of claim 1 wherein R is of type C.

10. The process of claim 9 wherein the compound of Formula I is t-butyl(±)-erythro(E)-7-[3'-(4''-fluorophenyl)-1'-(1''-methylethyl)-1H-indol-2'-yl]-3,5-dihydroxy hept-6-enoate and the compound of Formula II is t-butyl(±)-(E)-7-3'-(4''-fluorophenyl)-1'-(1''-methylethyl)-1H-indol-2'-yl]-5-hydroxy-3-oxo hept-6-enoate.

11. The process of claim 2 wherein the compound of Formula III is prepared by reacting a trialkylborane of formula V:

B(R₃)₃      V in which R₃ is as defined, under essentially anhydrous conditions, with an alcohol of formula VI:

R₄OH      VI in which R₄ is as defined.

12. The process of claim 11 in which R₃ is ethyl and R₄ is methyl.

13. The process of claim 11 which is carried out in a reaction medium consisting essentially of from 3 to 6 parts of tetrahydrofuran per part of part by volume of an alcohol.

14. The process of claim 13 which is carried out in a reaction medium consisting essentially of from 3 to 4 parts of tetrahydrofuran per part by volume of an alcohol.

15. The process of claim 13 wherein the molar ratio of sodium borohydride to the compound of Formula II is about 1.1:1 to 1.5:1.

16. The process of claim 13 wherein the molar ratio of the compound of Formula III to the compound of Formula II is at least about 0.5:1.

17. The process of claim 16 wherein the molar ratio of the compound of Formula III to the compound of Formula II is 0.7:1 to about 1.5:1.

18. The process of claim 17 wherein wherein R is of type C and X is CH=CH—.

19. The process of claim 1 wherein in step (b), the reaction medium is maintained at a temperature of about −100°−−40° C.

20. The process of claim 19 wherein in step (b), the reaction medium is maintained at a temperature of about −78°−−70° C.

21. The process of claim 14 wherein in step (b), the reaction medium is maintained at a temperature of about −78°−−70° C.

22. A process for synthesizing compounds of the formula:

$$\overset{\downarrow}{\underset{}{R-X-CH-CH_2-CH-CH_2-COOR_1}} \quad \text{I}$$

(with OH above each CH)

from compounds of the formula:

$$R-X-\underset{|}{\overset{Z_1}{C}}-CH_2-\underset{|}{\overset{Z_2}{C}}-CH_2-COOR_1 \quad \text{II}$$

wherein
X is —CH₂—CH₂— or —CH=CH—,
Z₁ and Z₂ are either =O or

provided that Z₁ and Z₂ are not the same,
R₁ is an ester group inert to the reaction conditions, and
R is an organic radical having groups which are inert under reducing conditions, comprising:

a. providing a reaction medium comprising sodium borohydride and an effective amount of a compound of Formula III:

R₄O—B(R₃)₂      III wherein R₃ is a primary or secondary alkyl having from 2 to 4 carbon atoms; and R₄ is allyl or alkyl having from 1 to 4 carbon atoms; and b. treating a compound of Formula II with said reaction medium under conditions suitable for formation of a cyclic boronate compound and/or boron complex of a compound of Formula I, wherein said cyclic boronate complex is formed; and c. cleaving the product of step (b) to obtain the corresponding compound of Formula I.

23. The process of claim 22 wherein the reaction medium comprises about 3 to 6 parts of tetrahydrofuran to 1 part by volume of an allyl alcohol or lower alcohol having 1 to 4 carbon atoms.

24. The process of claim 18 wherein R₁c is i-propyl, R₂c is 4-fluorophenyl, and R₃c and R₄c are each H.

25. The process of claim 16 wherein R is Type H and X is CH=CH.

26. The process of claim 25 wherein R₁h is i-propyl, R₂h is 4-fluorophenyl, and R₃h is phenyl.

27. The process of claim 18 wherein the compound of Formula I is t-butyl (±)-erythro-(E)-7-[3'-(4''-fluorophenyl)-1'-(1''-methylethyl)-indol-2'-yl]-3,5-dihydroxy-hept-6-enoate.

28. The process of claim 18 wherein the compound of Formula I is methyl (±)-erythro-(E)-7-[3'-(4''-fluorophenyl)-1'-(1''-methylethyl)-indol-2'-yl]-3,5-dihydroxy-hept-6-enoate.

29. The process of claim 18 wherein the compound of Formula I is t-butyl (+)-erythro-(E)-7-[1'-(4''-fluorophenyl)-4'-(1''-methylethyl)-2'-phenyl-1H-imidazol-5'-yl]-3,5-dihydroxy-hept-6-enoate.

* * * * *